United States Patent [19]

Stetter

[11] Patent Number: 5,714,373
[45] Date of Patent: Feb. 3, 1998

[54] THERMOCOCCUS AV4 AND ENZYMES PRODUCED BY THE SAME

[75] Inventor: Karl O. Stetter, Strasse, Germany

[73] Assignee: Recombinant BioCatalysis, Inc., Sharon Hill, Pa.

[21] Appl. No.: 394,479

[22] Filed: Feb. 27, 1995

[51] Int. Cl.$^6$ ........................................ C12N 1/20
[52] U.S. Cl. ........................... 435/235.1; 435/243
[58] Field of Search .......................... 435/252.1, 243

[56] References Cited

U.S. PATENT DOCUMENTS

| | | | |
|---|---|---|---|
| 5,177,013 | 1/1993 | Usui et al. | 435/176 |
| 5,202,260 | 4/1993 | Yee et al. | 435/280 |
| 5,232,843 | 8/1993 | Bosley et al. | 435/135 |
| 5,290,694 | 3/1994 | Nakanishi | 435/198 |

FOREIGN PATENT DOCUMENTS

| | | |
|---|---|---|
| 0305216 | 8/1988 | European Pat. Off. . |
| 0571049 | 2/1989 | European Pat. Off. . |
| WO91/19791 | 12/1991 | WIPO . |
| WO91/19792 | 12/1991 | WIPO . |

OTHER PUBLICATIONS

Bertolini, M., "Polymorphism in the Lipase Genes of *Geotrichum candidum* Strains", *Eur. J. Biochem.* 1994, 219, 119–125.
Derewenda, Z., "Structure and Function of Lipases", *Advances in Protein Chemistry* 1994, 45, 1–52.
Gormsen, E. et al. "Lipolase™. A Lipase for the Detergent Industry", (1991). Biotechnology International, London: Century Press pp. 280,282,283,285–287.
Hardwood, John, "The Versatility of Lipases for Industrial Uses", *TIBS* 1989. 14: 125–126.
Kobayashi, T. et al., "*Thermococcus profundus* sp. nov., A New Hyperthermophilic Archaeon Isolated form a Deepsea Hydothermal Vent", *System. Appl. Microbiol.* 1994, 17, 232–236.
Jaeger, K. -E. et al."Bacterial Lipases", *FEMS Microbiology Reviews* 1994, 15, 29–63.
Nagao, T. et al., "Cloning and Sequencing of Two Chromosomal Lipase Genes from *Geotrichum candidum*", *J. Biochem.* 1993, 113, 776–780.
Neuner, A. et al., "*Thermococcus litoralis* sp. nov. : A New Species of Extremely Thermophilic Marine Archaebacteria", *Arch. of Microb.* 1990, 153, 205–207.
Norin, M. et al., "Theiretical Studies of *Rhizomucor miehei* Lipase Activation ", *Protein Engineering* 1993, 6 (8), 855–863.
Taipa, M.A. et al., "Purification of Lipases", *J. of Biotechnology* 1992, 26, 111–142.
Gonzalez et al. (1995). Arch. Microbiol. 164: 159–164.
Antoine et al. (1995) Current Microbiol. 31: 186–192.
Keller et al. (1995). Arch. Microbiol. 164: 390–395.
Kwak et al. (1995) Biosci. Biotech. Biochem. 59: 1666–1669.

*Primary Examiner*—Robert A. Wax
*Assistant Examiner*—G. E. Bugalsky
*Attorney, Agent, or Firm*—Woodcock Washburn Kurtz Mackiewicz & Norris LLP

[57] ABSTRACT

An isolated preparation of a new species of bacteria, Thermococcus AV4, is disclosed. Also described is a substantially pure preparation of a protease and a substantially pure preparation of a lipase encoded by Thermococcus AV4.

5 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (ii) MOLECULE TYPE: DNA (genomic)

(xi) SEQUENCE DESCRIPTION: SEQ ID NO:1:

GTAAAACGAC GGCCAGT　17

THERMOCOCCUS AV4 AND ENZYMES PRODUCED BY THE SAME

FIELD OF THE INVENTION

The field of the invention is thermophilic bacteria and enzymes with protease and lipase activity produced from the same.

BACKGROUND OF THE INVENTION

The Archaebacteria comprise a group of unusual prokaryotic organisms which are separated from all other prokaryotes in that they are believed to have diverged in evolution from the original predecessor of life prior to all other bacteria. They are also unique in that they lack a true peptidoglycan cell wall and are found in habitats characterized by environmental extremes. Included in the Archaebacteria is the genus Thermococcus.

Thermostable protease enzymes are useful in a variety of industrial applications. Heretofore, useful enzymes include those isolated from *Bacillus subtilis*, *Bacillus lichenformis* and from alkalophilic bacilli. In addition, PCT Patent Application WO 91/19792 discloses production of thermal stable proteases from *Thermococcus celer*, *Thermococcus stetteri* and *Thermococcus litoralis*, and PCT Patent Application WO 91/19791 discloses production of a thermal stable protease from *Staphylothermus marinus*.

Thermostable lipase enzymes are also useful in a variety of industrial applications. Useful lipases derived from microbial sources are reviewed in Taipa et al. (J. Biotechnology 26:111–142, 1992), Derewenda (Adv. Protein Chemistry 45:1–52, 1994) and in Jaeger et al. (FEMS Microbiology Rev. 15:29–63, 1994).

Because of the tremendous breadth of applications for which thermostable proteases and lipases are useful, there remains a need for new and better thermostable proteases and lipases which are capable of performing numerous and varied functions in industry. Novel bacteria capable of producing such enzymes in large quantities are also needed. The present invention is directed to these as well as other ends.

SUMMARY OF THE INVENTION

The invention features an isolated preparation of a new species of Archaebacteria, Thermococcus AV4. Also included is a substantially pure preparation of a protease and a substantially pure preparation of a lipase encoded by Thermococcus AV4. Also included in the invention is an isolated DNA encoding a Thermococcus AV4 protease and isolated DNA encoding a Thermococcus AV4 lipase.

DETAILED DESCRIPTION OF THE INVENTION

Figure 1:
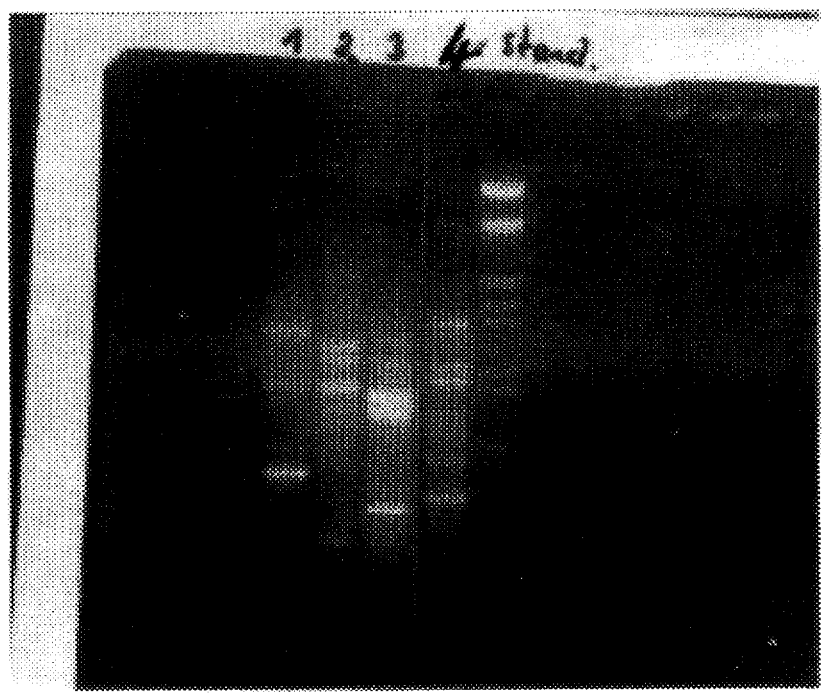
FIG. 1 is a photograph of a gel depicting the Polymerase Chain Reaction (PCR) profile for various species of Thermococcus using the M13 forward primer 5'- GTAAAAC-GACGGCCAGT -3'. Lane 1: *Thermococcus litoralis*; lane 2: *Thermococcus celer*; lane 3: *Thermococcus stetteri*; lane 4: Thermococcus AV4.

The invention provides a novel species of Thermococcus, Thermococcus AV4, which as shown herein, is capable of producing at least one thermostable protease and at least one thermostable lipase useful in industrial applications. The Thermococcus AV4 of the invention is provided as an isolated preparation by which is meant a preparation of Thermococcus AV4 which is separated from native components with which it is naturally associated. Such native components include naturally associated soil or other habitat substances and other bacteria and microorganisms, such as fungi and algae.

Other members of the species of Thermococcus AV4 which may also produce useful proteases and lipases may be isolated in a manner similar to that described herein for the prototype AV4. Essentially, a sample is obtained from an extreme environment. Bacteria having similar morphological, biochemical, physiological and/or molecular characteristics to Thermococcus AV4, such as those described herein, are isolated by serial dilution under growth conditions also similar to those described herein, which growth conditions are known to promote growth of Thermococcus AV4. Such isolated organisms comprise those suspected of being Thermococcus AV4-like organisms.

A PCR profile may be obtained for each organism suspected of being a Thermococcus AV4-like organism. Based on this profile, Thermococcus AV4-like organisms may be identified and characterized. This technology is standard in the art and is described, for example, in Welsh et al. (PCR Protocols, $2^{nd}$ Edition; J. J. Sninski et al., Eds., 1994). In addition, a 16S rRNA sequence analysis may be performed for each organism suspected of being a Thermococcus AV4-like organism. Based on the sequence of the 16S rRNA, Thermococcus AV4-like organisms may be identified and characterized. Further, once an organism is suspected of being a Thermococcus AV4-like organism, DNA may be obtained from that organism using standard technology and may be compared, using hybridization technology, with the Thermococcus AV4 of the invention. Methods for DNA extraction and comparison by hybridization are well known procedures which are standard in the art of molecular biology and are described, for example, in Sambrook et al., Molecular Cloning: A Laboratory Manual, Cold Spring Harbor, N.Y. (1989).

An organism may be classified as a Thermococcus AV4-like organism by having the following characteristics. Thermococcus AV4 is a member of the group Thermococcales, which represents a branch-off within the Euryarchaeota. Thermococcus AV4 is characterized as an anaerobic heterotroph which grows on yeast extract, peptone, meat extract and tryptone. This organism derives its energy from fermentative processes producing acids such as acetic acid, propionic acid, butyric acid, each of which are fermentative end-products of amino acid degradation. Thermococcus AV4 grows optimally at about 85° C. and maximally at about 94° C. at a pH range of about 4.0 to 9.0, having a pH optimum of about 6.0. The organism grows in the presence of gaseous phases $N_2$ and $N_2/CO_2$. During growth of the organism, when elemental sulfur is present in addition to gases $N_2$, $N_2/CO_2$ or $H_2$, elemental sulfur is reduced to $H_2S$. This reduction of elemental sulfur serves to eliminate redox-equivalents ($H_2$) in the growth environment which inhibit growth of the organism.

As described herein, the novel Thermococcus AV4 species of the invention is characterized as having a PCR profile which is different from that of other Thermococcus species and which is better characterized by the unique profile shown in FIG. 1. Also included in the present invention are other Thermococcus AV4-like organisms which share substantial overall DNA homology with the Thermococcus AV4 disclosed herein. Organisms within a genus which share substantial overall DNA homology with each other, and which have other characteristics in common such as morphological, biochemical, physiological and/or molecular characteristics, are also considered to be members of the same species within that genus. Typically, two organisms may be considered to be related to each other at the species level and have substantial overall DNA homology when they share at least about 70% DNA homology, although at least about 75%, 80%, 85%, 90%, 95% or 100% homology are preferred. By overall DNA homology between two organisms is meant homology between the genomes of the two organisms as opposed to homology between portions of their genomes. The former type of homology is typically determined by standard $C_o t$ curve-type analysis, while the latter type of homology refers to the actual sequence homology between, for example, the 16S rRNA gene sequences of two organisms. As a general matter, it should be noted that a value of approximately 70% overall DNA homology as determined by $C_o t$ curve-type analysis, generally indicates approximately 95% actual sequence homology between two organisms.

Also included in the present invention are other Thermococcus AV4-like organisms which have a substantially similar 16S rRNA sequence to that of the Thermococcus AV4 described herein. Comparison of 16S rRNAs from different bacterial isolates is well known in the art. In general, for bacterial isolates having the same general morphological, biochemical, physiological and/or molecular characteristics, when there is less than about 10% sequence difference between the 16S rRNAs of two isolates, they are considered to be within the same genus; when there is less than about 5% difference in the 16S rRNA sequences, they are considered to be members of the same species. Thus, by substantially similar 16S rRNA sequence as used herein, is meant a 16S rRNA sequence which is at least about 95% homologous with the 16S rRNA sequence of the Thermococcus AV4 described herein.

Using the criteria described herein, organisms which are designated as members of the genus Thermococcus species AV4, and which have a 16S rRNA sequence characteristic of Thermococcus AV4, and further which share substantial (at least about 70%) overall DNA homology with Thermococcus AV4 DNA, are designated as members of Thermococcus AV4 species. Thus, by the term "Thermococcus AV4" as used herein, is meant all other heretofore unknown members of Thermococcus AV4 species having an DNA base composition similar to that described herein, a 16S rRNA sequence substantially similar to the 16S rRNA sequence of Thermococcus AV4 described herein, and further which share substantial overall DNA homology with Thermococcus AV4 DNA. The preferred strain of Thermococcus AV4 is the Thermococcus AV4 disclosed herein.

As used herein, the term homology as it refers to sequence homology, refers to the subunit sequence similarity between two polymeric molecules e.g., between two nucleic acid molecules, e.g., between two DNA molecules. When a subunit position in both of the two molecules is occupied by the same monomeric subunit, e.g., if a position in each of two nucleic acid molecules is occupied by adenine, then they are homologous at that position. The homology between two sequences is a direct function of the number of matching or homologous positions, e.g., if half (e.g., 5 positions in a polymer 10 subunits in length) of the positions in two nucleic acid sequences are homologous then the two sequences are 50% homologous; if 70% of the positions, e.g., 7 out of 10, are matched or homologous, the two sequences share 70% homology. By way of example, the nucleic acid sequences GAATTC and GAAGGT share 50% homology.

By substantial overall DNA homology is meant at least about 70% overall DNA homology which is an indication of about 95% actual sequence homology. By similar 16S rRNA sequence is meant at least about 95% homology. By PCR profile similar to that of Thermococcus AV4 is meant a PCR profile substantially similar to that shown in lane 4 of FIG. 1, using the primer 5'-GTAAAACGACGGCCAGT-3' [SEQ ID NO: 1] and the reaction conditions described herein.

The invention also provides a novel protease enzyme encoded by Thermococcus AV4. Protease enzymes are useful in a variety of industrial applications, including, but not limited to, detergent-based activity, depilating hides, deproteinization of rubber, haze removal in brewing, fish processing, meat tenderization, baking, silver recovery in photographic applications, and removal of protein from xanthum gum fermentation. In the detergent industry, for example, proteases may used to complement the activity of the detergent at temperatures which ordinarily do not support enzyme activity. Thermococcus AV4 protease has an unusual thermostability when compared to other proteases. Thus, this enzyme is a good candidate for industrial applications requiring high temperatures, such as laundering (detergents), fish stick water hydrolysis, etc.

The invention further provides a novel lipase enzyme encoded by Thermococcus AV4. Lipases are also useful in industrial applications, for example, in the detergent industry, in fat modification, fat emulsions, cocoa butter, flavoring of milk and cheese products, and in generating solutions of organic acids via esterification in organic media. Since the Thermococcus AV4 lipase of the invention has an unusual temperature stability, this enzyme is also a good candidate for applications requirement higher temperatures, such as laundering, etc. In addition, lipases have many different applications in the chemical industry. For example, lipases are useful for kinetic resolution of phenylcyclohexanone oxime esters, resolution of racemic acids and alcohols, transesterification of oils, etc.

In general, to obtain a preparation of Thermococcus AV4 protease or lipase, Thermococcus AV4 cells are disrupted by sonication. The lysate is clarified by centrifugation following which ion exchange gel filtration/affinity chromatography is performed.

As used herein, the phrase substantially pure preparation describes a preparation of a compound, e.g., a protease or a lipase, which has been substantially separated from components which accompany it in its natural state. In accordance with the present invention, a preparation of a compound is substantially pure when at least about 5%, preferably at least about 10%, more preferably, at least about 20%, even more preferably, at least about 40%, still more preferably, at least about 60%, even still more preferably, at least about 80%, more preferably, at least about 90%, and most preferably greater than 90% of the total material (by volume, by wet or dry weight, or by mole percent or mole fraction) in a sample is the compound of interest. Purity can be measured by any appropriate method, as will be well understood by one skilled in the art, e.g., in the case of polypeptides, by column chromatography, polyacrylamide gel electrophoresis, or HPLC analysis.

The invention also provides an isolated DNA sequence encoding Thermococcus AV4 protease and an isolated DNA sequence encoding Thermococcus AV4 lipase. To clone DNA encoding the protease or lipase of the invention, a genomic DNA expression library of Thermococcus AV4 is first generated using standard technology and is screened for protease and lipase activity. Positive clones are selected and further characterized also using standard technology described, for example, in Sambrook et al. (Molecular Cloning: A Laboratory Manual, Cold Spring Harbor, N.Y.). Alternatively, protease or lipase enzymes are purified to a resolvable band on an acrylamide gel. An N-terminal amino acid sequence is obtained from which a DNA primer is generated. This primer is then used to locate a clone within the library encoding the desired enzyme, which clone is then purified and characterized. In yet another cloning scheme, the PCR primer obtained as described may be used to directly clone the desired sequence from genomic DNA by hybridization of the primer to restriction enzyme fragments of genomic DNA which when hybridized may then cloned via the addition of linkers and subsequent amplification. Each of the cloning procedures described herein are standard procedures readily available to molecular biologists. Moreover, once the sequence is identified, a DNA sequence may be synthetically generated using standard procedures well known in the art.

By isolated DNA sequence, as used herein, is meant a DNA sequence which has been purified from the sequences which flank it in a naturally occurring state, e.g., a DNA sequence which has been removed from the sequences which are normally adjacent to the DNA sequence, i.e., those sequences which are adjacent to the DNA sequence in the genome in which it naturally occurs. The term also applies to a DNA sequence which has been substantially purified from other components which naturally accompany it, such as RNA, protein and lipid, i.e., those components which naturally accompany it in a cell. Isolated DNA sequence also denotes a synthetically prepared DNA sequence corresponding to the cloned sequence.

The following provides some examples of the present invention. These examples are not to be considered as limiting the scope of the appended claims.

EXAMPLES

Example 1.

Isolation and Identification of Thermococcus AV4

The novel Thermococcus species of the invention, Thermococcus AV4, was isolated from a serially diluted sample obtained from the Guaymas basin in the Gulf of California in Mexico. The sample was obtained at the following location: latitude 27° 00' North; Longitude 111°, 24' West at a depth of 2000 meters.

The organism grows under anaerobic conditions in medium containing yeast extract, peptone, meat extract and tryptone. The medium in which the organism grows best is called Marine Broth 2216, modified (ZoBell, 1941, Difco Manual, 10$^{th}$ issue). The components of this medium are as follows: NaCl (19.45 g); $MgCl_2$ ×$6H_2O$ (12.6 g); $Na_2SO_4$ (3.24 g); $CaCl_2$ (2.38 g); KCl (0.55 g); $NaHCO_3$ (0.16 g); KBr (0.08 g); $SrCl_2$ ×$6H_2O$ (57 mg); $H_3BO_4$ (22 mg); $Na_2HBO_4$ (10 mg); Na-meta-silicate (4 mg); NaF (2.4 mg); $KNO_3$ (2.0 mg); Resazurine (0.1% solution) (1 ml); $H_2O$ distilled (add to 1 liter); yeast extract (0.4%); peptone (0.5%); elemental sulfur (1%).

Thermococcus AV4 is resistant to ampicillin, chloramphenicol, kanamycin, penicillin G, streptomycin and vancomycin (each at concentrations of about 100 µg/ml); however, growth of this organism is inhibited by rifampicin at about 100 µg/ml.

Optimal growth of Thermococcus AV4 occurs at a temperature of about 85° C.; the maximum growth temperature for this organism being about 94° C. The organism grows best at about pH 6.0, but is capable of growth at a pH ranging from about 4.0 to about 9.0.

A comparison of Thermococcus AV4 with all known members of the genus Thermococcus was performed by PCR analysis. The results of this comparison are shown in FIG. 1. The species used in the comparison include *Thermococcus celer*, *Thermococcus stetteri*, and *Thermococcus litoralis*. Based upon the appearance of the PCR product following agarose gel electrophoresis, Thermococcus AV4 represents a new species within this genus.

The PCR experiment was performed essentially as described by Welsh et al. (PCR Protocols, 2$^{nd}$ Edition; J. J. Sninski et al., Eds., 1994). A 50 µl reaction volume contained: 10× Taq buffer (5 µl); Forward primer (5.39 µl, approximately 50 pmol); Nucleotides at a 1:1:1:1 ratio (4 µl); $H_2$ (30.36 µl); Taq polymerase (0.25 µl, 5 U/µl); DNA (5 µl, a concentration between 2 and 26 ng/ml). The primer used was 5'-GTAAAACGACGGCCAGT-3'. Two cycles of reaction were conducted for 5 minutes at 94° C., 5 minutes at 40° C. and 5 minutes at 72° C. Forty cycles of reaction were conducted for 1 minute at 94° C., 1 minute at 40° C. and 2 minutes at 72° C. The reaction was stopped by reducing the temperature of the mixture to 4° C., and the products were separated on a conventional 1.5% agarose gel.

Deposit of Thermococcus AV4

Under the terms of the Budapest Treaty on the International Recognition of the Deposit of Microorganisms for the Purpose of Patent Procedure, deposit of Thermococcus AV4 has been made with the American Type Culture Collection (ATCC) of Rockville, Md., USA, where the deposit was given ATCC Accession Number 55659.

Applicant's assignee, Industrial BioCatalysis, Inc., represents that the ATCC is a depository affording permanence of the deposit and ready accessibility thereto by the public if a patent is granted. All restrictions on the availability to the public of the material so deposited will be irrevocably removed upon granting of a patent. The material will be available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Example 2.

Isolation and Characterization of Thermococcus AV4 Protease and Lipase.

One gram (wet weight) of Thermococcus AV4 was suspended by pipetting and vortexing, in 10 mM Tris, pH 7.6, 1 mM EDTA, pH 8.0, 1 mM each of dithiothreitol and Benzamidine, and 1 g/ml each of Pepstatin A and Aprotinin.

The organisms so suspended were lysed by sonication (2×30 second pulses using a microtip). Cell debris was separated from cell supernatant by centrifugation at 10K in an SS34 Sorvall rotor.

Figure 2:
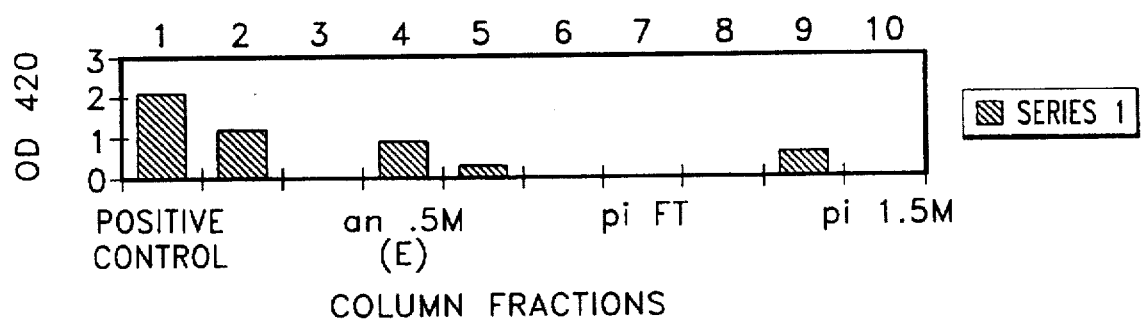
FIG. 2 is a graph depicting protease activity in lysates of Thermococcus AV4.

Protease activity was assessed in the lysed cell pellet as follows: Each reaction mixture contained 248 µl of distilled water, 120 µl of Tris, pH 9.0, 120 µl 10% Azocasien, and 12 µl mM $CaCl_2$, and 50 µl of sample. The components of the reaction were mixed together on ice followed by incubation for 2 hours at 65° C. The reaction was stopped by placing the mixture on ice. Trichloroacetic acid (600 µl of a 10% solution) was added and the mixture was vortexed and centrifuged in a microfuge. The supernatant was transferred to a cuvette containing 200 µl of a 1.8M NaOH and the optical density was determined at 420 nm. Protease activity in fractions obtained from lysed Thermococcus AV4 is shown in FIG. 2.

Figure 3:
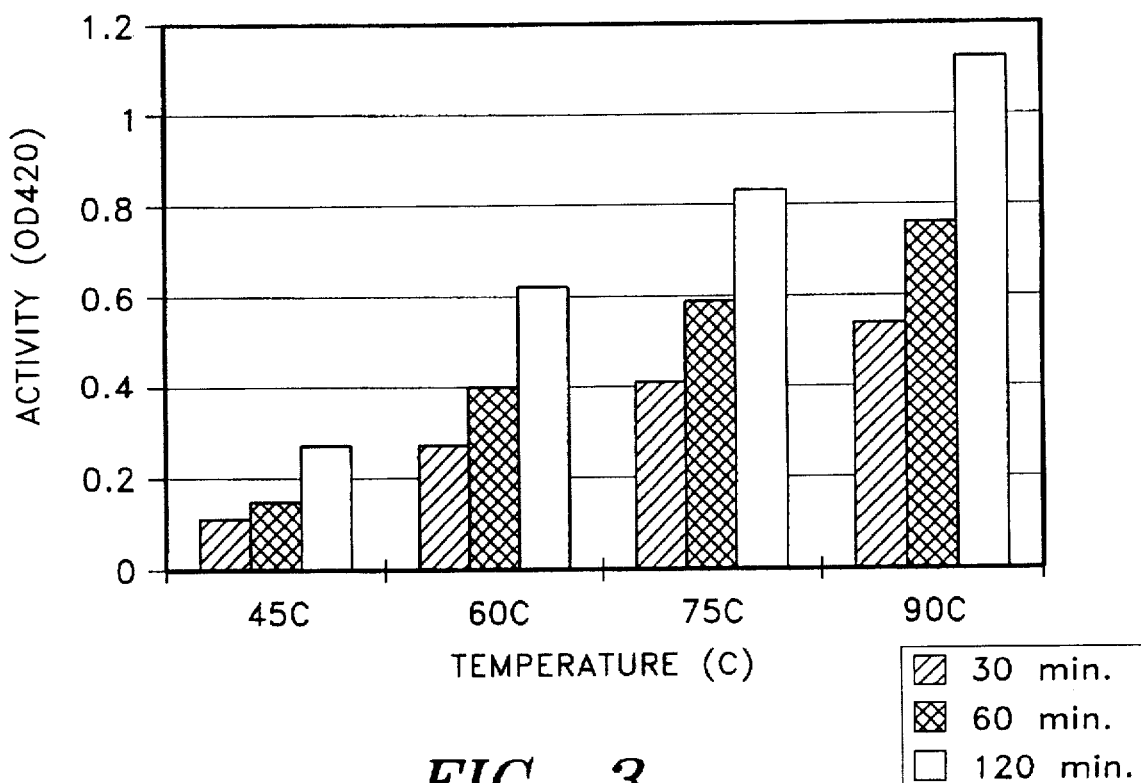
FIG. 3 is a graph depicting the effect of temperature on protease activity assessed at pH 10.0 in lysates of Thermococcus AV4.
Figure 4:
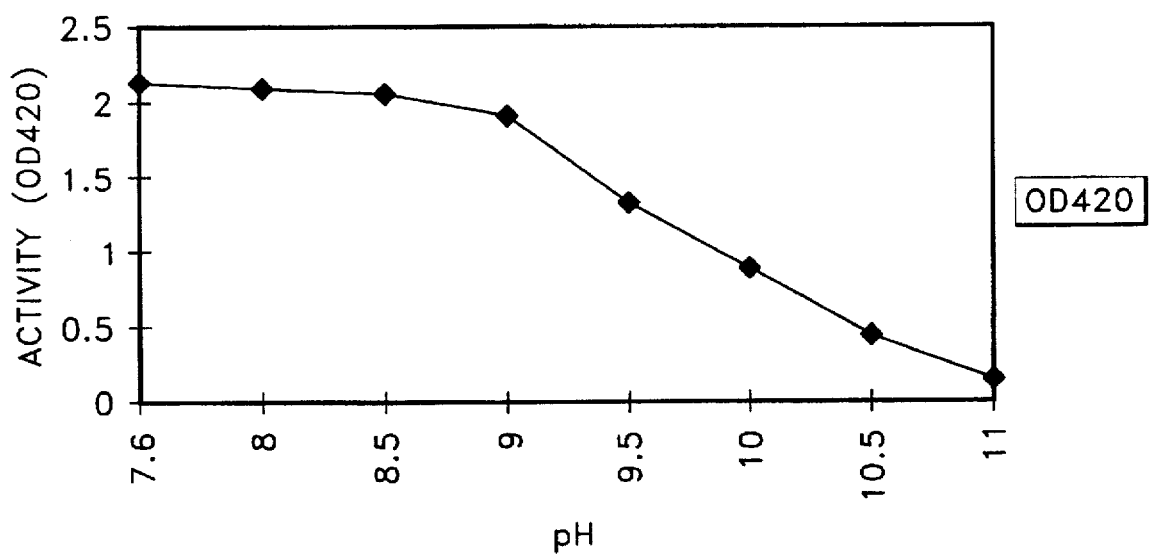
FIG. 4 is a graph depicting the effect of pH on Thermococcus AV4 protease activity.

The effect of temperature on Thermococcus AV4 protease activity was assessed by incubation of Thermococcus AV4 protease at the temperatures and for the times indicated in FIG. 3. All incubations were conducted at pH 10.0. Further, the effect of pH on Thermococcus AV4 protease activity is depicted in FIG. 4. In this experiment, the temperature used was 90° C.

Partial purification of the enzyme was also conducted as follows: A sample of crude lysate containing Thermococcus AV4 protease was loaded onto a Porous PI/M weak anion exchange column (PerSeptive Biosystems). The column was equilibrated in a buffer containing 10 mM Tris, 10 mM Bis-Tris-Propane and 100 mM NaCl, at pH 9.0. Fractions were step eluted with 0.5M, 1.0M and 1.5M NaCl in the same buffer. Protein eluted in the 1M NaCl fraction. Elution of protein was assessed by absorption at 280 nm. Peak fractions of protein were pooled and protease activity was assessed and found to have the characteristics described herein.

In summary, a protease has been isolated and identified in a novel species of Thermococcus, Thermococcus AV4, which protease has an optimum temperature range of between about 60° C. and about 90° C. and an optimum pH range of between about pH 7.5 and pH 9.0. A substantially pure preparation of a protease and a lipase encoded by Thermococcus AV4 and an isolated DNA encoding a Thermococcus AV4 protease and lipase are encompassed in the present invention.

By temperature optimum, as used herein, is meant the temperature at which the enzyme of the invention is maximally active. By pH optimum, as used herein, is meant the pH at which the enzyme of the invention is maximally active.

Within this optimum range of temperature, the temperature may range anywhere from about 60° C. to 61° C., 62° C., 63° C. . . . 88° C., 89° C. and about 90° C. with any and all integers and tenths of integers therebetween included therein.

Within this optimum pH range, the pH may range anywhere from about pH 7.5, pH 7.6, pH 7.7 . . . pH 8.8, pH 8.9 and about pH 9° with any and all integers and tenths of integers therebetween included therein.

Thermococcus AV4 also produces a lipase. When crude extracts of this organism were assayed in a lipase assay, lipase activity was observed. The assay which was conducted is a liquid titrimetric assay which determines the amount of lipase activity in a sample. Lipase activity is measured as the hydrolysis of triglycerides to diglycerides and fatty acids, monoglycerides and glycerol. The amount of fatty acid formed is determined by titration with sodium hydroxide. Other assays for lipase may also be employed including for example, those readily available from Sigma Chemical Co. St. Louis. Mo. (Sigma Prod. Nos. L-0763 and L-3126) .

The liquid titrimetric assay is performed essentially as follows: Materials for the assay include Sigma lipase substrate #800-1; 200 mM Tris-HCl at the desired pH; 100% ethanol and thymolphthalein indicator solution, Sigma #800-3. To perform the assay, 650 µl of assay mix containing 125 µl of $H_2O$, 500 µl of lipase substrate and 50 µl of 200 mM Trizma are mixed on ice. The reaction mixture is divided into two tubes. One set remains on ice, while the other is incubated at the desired temperature for 2 hours. The reaction is stopped by the addition of 75 µl 100% ethanol and one drop of the indicator is added. The mixture is vortexed and 10 µl 10.05M NaOH is added dropwise with mixing until a light blue color change is observed. The difference between the amount of NaOH required to effect the color change between the incubated and unincubated sample is an indication of the amount of lipase activity present in the sample.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated preparation of Thermococcus AV4.

2. An isolated preparation of Thermococcus AV4 which produces a protease wherein the temperature optimum of said protease is from about 60° to about 90° C.

3. An isolated preparation of Thermococcus AV4 according to claim 2 wherein the pH optimum of said protease is from about pH 7.5 to about pH 9.0.

4. An isolated preparation of Thermococcus AV4 according to claim 2 wherein the temperature optimum of said protease is from about 60° C. to about 90° C. and the pH optimum of said protease is from about pH 7.5 to about pH 9.0.

5. An isolated preparation of Thermococcus AV4 having all the identifying characteristics of ATCC Accession Number 55659.

* * * * *